United States Patent [19]

Philippon et al.

[11] Patent Number: 5,229,135
[45] Date of Patent: Jul. 20, 1993

[54] SUSTAINED RELEASE DILTIAZEM FORMULATION

[75] Inventors: Francis Philippon, Treon; Marie-Sylvie Boutin, St. Gemme; Gerard Cousin, Gallardon; Etienne Bruna, Chartres, all of France

[73] Assignee: Prographarm Laboratories, Chateauneuf-Fn-Thymerais, France

[21] Appl. No.: 797,496

[22] Filed: Nov. 22, 1991

[51] Int. Cl.$^5$ .................. A61K 9/24; A61K 31/55
[52] U.S. Cl. .................. 424/494; 424/470; 424/471; 424/480
[58] Field of Search ........... 424/489, 490, 491, 492, 424/493, 494

[56] References Cited

U.S. PATENT DOCUMENTS

| | | | |
|---|---|---|---|
| 4,891,230 | 1/1990 | Geoghegan et al. | 424/461 |
| 4,894,240 | 1/1990 | Geoghegan et al. | 424/497 |
| 4,898,737 | 2/1990 | Ranoz et al. | 424/468 |

Primary Examiner—Thurman K. Page
Assistant Examiner—Neil Levy
Attorney, Agent, or Firm—Caesar, Rivise, Bernstein, Cohen, Pokotilow, Ltd.

[57] ABSTRACT

A sustained release diltiazem formulation for oral administration comprising a pellet having a central sugar sphere a plurality of alternating first and second layers surrounding the sphere to form a core, the first layer comprising a water soluble pharmaceutically acceptable polymeric material and the second layer comprising diltiazem or a pharmaceutically acceptable salt thereof and an outer membrane surrounding the plurality of layers. The outer membrane comprises first inner membrane layers of ethylcellulose. The outer membrane also comprises an outer membrane coating of a water insoluble pharmaceutically acceptable polymeric material, a plasticizer and a lubricant, in from one to five or more layers. The number of layers and the coating of the two outer membrane layers are effective to permit the release of the diltiazem from the pellet at a rate allowing controlled absorption thereof over a twelve or twenty four hour period following oral administration, the rate being measured in vitro as a dissolution rate of the pellet, which when measured in an aqueous solution in a paddle apparatus according to United States Pharamcopeia XXII, substantially corresponds to the following dissolution pattern: from 15 to 40% of the total diltiazem is released after 4 hours of measurement; from 40 to 70% of the total diltiazem is released after 8 hours of measurement; from 50 to 85% of the total diltiazem is released after 12 hours of measurement; and from 70 to 100% of the total diltiazem is released after 24 hours of measurement.

6 Claims, 1 Drawing Sheet

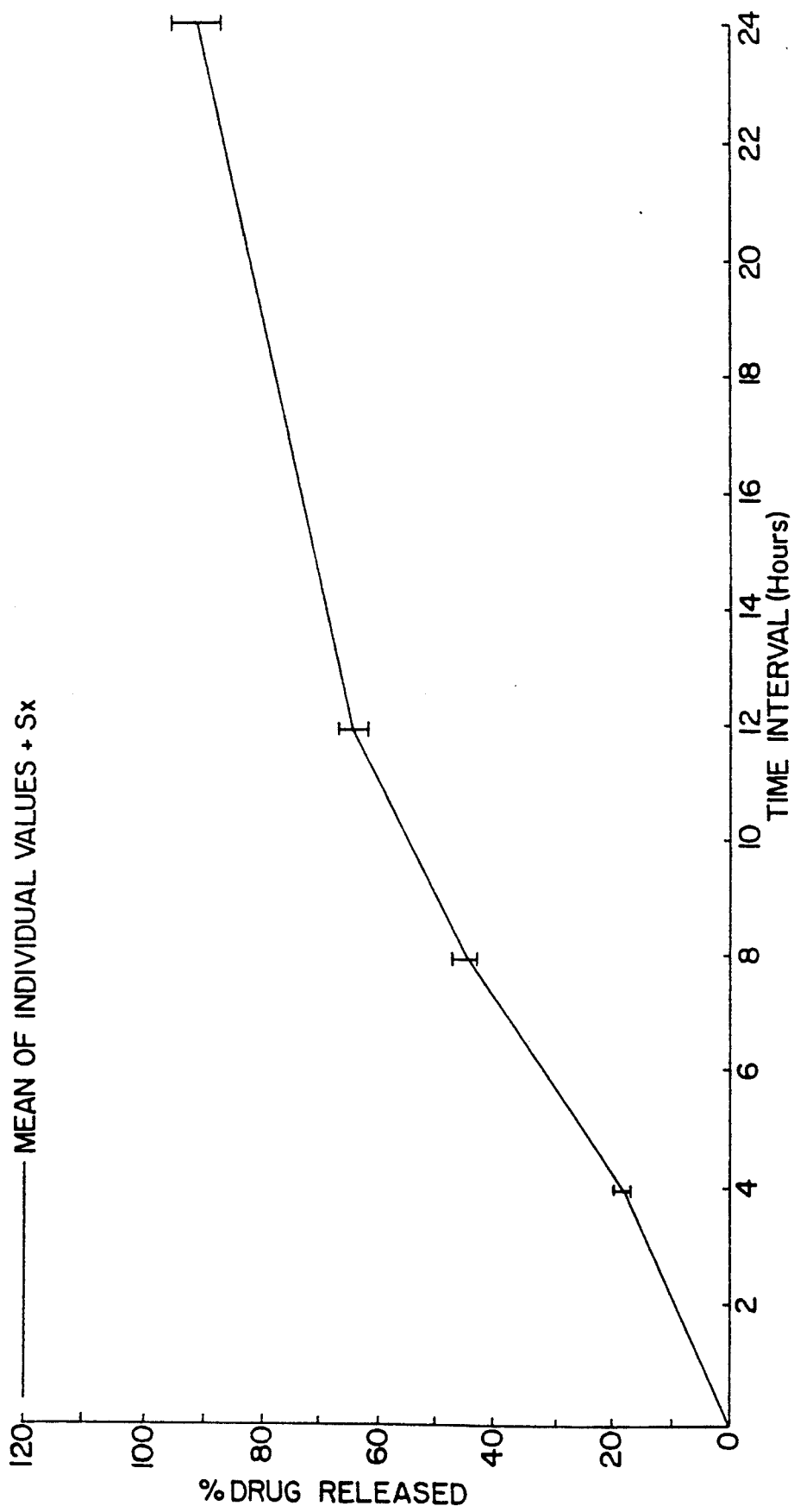

SUSTAINED RELEASE DILTIAZEM FORMULATION

BACKGROUND OF THE INVENTION

Diltiazem-cis-(+)-3-(acetyloxy)-5-[2-(dimethylamino)ethyl]-2,3-dihydro-2-)4-methoxyphenyl)-1,5-benzothiazepin-4(5H)-one hydrochloride, is a benzothiazine derivative which is a calcium ion influx inhibitor, i.e., a slow channel blocker or calcium antagonist. Diltiazem hydrochloride has a molecular weight of 450.98 and is a white to off-white crystalline powder, which is soluble in water, methanol, and chloroform.

Diltiazem hydrochloride has been shown to be useful in alleviating symptoms of chronic heart disease, particularly angina pectoris and myocardial ischemia, while displaying a low incidence of side effects. Diltiazem is conventionally administered orally as diltiazem hydrochloride.

Diltiazem is extensively metabolized by the liver and excreted by the kidneys and in bile. Although precise mechanisms of its anti-anginal actions are still being delineated, diltiazem is believed to act in the following ways. Diltiazem has been shown to produce increases in exercise tolerance, probably due to its ability to reduce myocardial oxygen demand. This is accomplished in reductions in heart rate and systemic blood pressure at submaximal and maximal exercise work loads. In animal models, diltiazem interferes with the slow inward (depolarizing) current in excitable tissue. It causes excitation-contraction uncoupling in various myocardial tissues without changes in the configuration of the action potential. Diltiazem produces relaxation of coronary vascular smooth muscle and dilation of both large and small coronary arteries at drug levels which cause little or no negative inotropic effect. The resultant increases in coronary blood flow (epicardial and subendocardial) occur in ischemic and non-ischemic models and are accompanied by dose-dependent decreases in systemic blood pressure and decreases in peripheral resistance.

Like other calcium antagonists, diltiazem decreases sinoatrial and atrioventricular conduction in isolated tissues and has a negative inotropic effect in isolated preparations. In the intact animal, prolongation of the AH interval can be seen at higher doses.

In humans, diltiazem prevents spontaneous and ergonovine-provoked coronary artery spasm. It causes a decrease in peripheral vascular resistance and a modest fall in blood pressure, and in exercise tolerance studies in patients with ischemic heart disease, reduces the heart rate-blood pressure product for any given work load.

Diltiazem is absorbed from the tablet formulation to about 80% of a reference capsule and is subject to an extensive first-pass effect, giving an absolute bioavailability (compared to intravenous dosing) of about 40%.

Various types of sustained release diltiazem formulations have been described in the literature ("The Use of Diltiazem Hydrochloride in Cardiovascular Disorders", McAuley and Schroeder, Pharmacotherapy, Vol. 2, No. 3, p. 121, May/June 1982) and in the following United States patents, the disclosures of materials used (to the extent pertinent) and manufacturing techniques (to the extent properly disclosed) which are incorporated by reference herein: U.S. Pat. Nos. 5,002,776, 4,960,596, 4,917,899, 4,894,240, 4,891,230, and 4,721,619. However, all but one of these (4,960,596) involve the use of organic acid which may have an irritating effect.

Accordingly, a need exists for a sustained release diltiazem formulation for twice daily administration which does not have an irritating effect and which has a satisfactory dissolution rate or pattern.

OBJECTS OF THE INVENTION

Accordingly, it is a general object of this invention to provide a sustained release diltiazem formulation which overcomes the disadvantages of the prior art.

It is a further object of this invention to provide a sustained release diltiazem formulation which is relatively easy and inexpensive to manufacture.

It is yet a further object of this invention to provide a sustained release diltiazem formulation which is suitable for twice daily administration.

It is yet another object of this invention to provide a sustained release diltiazem formulation which is suitable for once daily administration.

It is yet another object of this invention to provide a controlled absorption diltiazem formulation which has equivalent bioavailability relative to known diltiazem oral formulations.

SUMMARY OF THE INVENTION

These and other objects of this invention are achieved by providing a sustained release diltiazem formulation for oral administration comprising a pellet first comprising a sugar or sugar/starch sphere, a plurality of alternating first and second layers surrounding the sphere to produce a core, the first alternating layer comprising a water soluble pharmaceutically acceptable polymeric material and the second alternating layer comprising diltiazem or a pharmaceutically acceptable salt thereof to produce the core. Finally, first and second membrane layers are applied to the core. The first or innermost membrane layers are of coatings of a first water insoluble, pharmaceutically acceptable polymeric material, such as ethylcellulose with added talc or other lubricant. The second or outermost membrane layer is of a single, but relatively thick coating of a water insoluble pharmaceutically acceptable polymeric material, such as EUDRAGIT S 100 a plasticizer such as diethyl phthalate and talc or other lubricant.

The number of layers of the inner membrane and the outer membrane coating are effective to permit the release of the diltiazem from the core at a rate allowing controlled absorption thereof over an eight, twelve or twenty four hour period following oral administration, the rate being measured in vitro as a dissolution rate of the pellet which when measured in an aqueous medium utilizing a paddle apparatus according to United States Pharmacopeia XXII, substantially corresponds to the following dissolution pattern: from 15 to 40% of the total diltiazem is released after 4 hours of measurement; from 40 to 70% of the total diltiazem is released after 8 hours of measurement; from 50 to 85% of the total diltiazem is released after 12 hours of measurement; and from 70 to 100% of the total diltiazem is released after 24 hours of measurement.

DESCRIPTION OF THE DRAWING

Other objects and many attendant features of this invention will become readily appreciated as the same becomes better understood by reference to the following detailed description when considered in connection with the accompanying drawing wherein FIG. 1 is a graph of the dissolution rate of sustained released diltiazem hydrochloride expressed as percent of drug released versus time (hours) and graphed as the mean of the individual values+Sx, as measured by dissolving the 120 mg capsule sample in 900 mls of water in a paddle apparatus at 100 rpm according to United States Pharmacopeia XXII.

DETAILED DESCRIPTION OF THE PREFERRED EMBODIMENT

The sustained release diltiazem formulation of the present invention is comprised of a non-pareil seed or sphere having an average diameter of in the range of 0.4 mm to 0.7 mm and is comprised of neutral excipients such as sugar or sugar/starch. The microgranules produced in accordance with the present invention, preferably contain about 20 to 37% by weight of neutral core.

Applied to the core are a plurality of alternating layers of diltiazem or a pharmaceutically acceptable salt thereof, such as the hydrochloride applied by dusting of the powdered active ingredient, and a water soluble pharmaceutically acceptable polymeric material such as polyvinylpyrrolidone (PVP), such as grade PVP K 30. Also, other suitable water soluble polymers are polyethylene glycol or polyvinyl alcohol or mixtures of PVP and any of the foregoing. This multi-layer arrangement is accomplished in a conventional coating pan utilizing conventional methods such as spraying of the ingredients to form the plurality of successive layers of active ingredient and polymer. It should be emphasized that nothing else, such as an organic acid or talc is used in association with the diltiazem hydrochloride or PVP or other polymer.

A solution of the PVP is prepared in water or a solubilizing organic solvent (e.g., ethyl alcohol, acetone, isopropanol, water or a mixture thereof) and the central core is wetted with the PVP solution. A desired quantity of the diltiazem is projected or dusted upon the wetted core and then there is a short drying step. The operation of alternating PVP and diltiazem coating is repeated until the quantity of diltiazem corresponding to the desired dose is obtained. The concentration of the polymeric material in the solution is determined by the viscosity of the final solution. Preferably the ratio of inert core to diltiazem is between 1:1 and 1:10. The active core is obtained through a process which involves a certain number of cycles. Each cycle does not lead to an additional layer on the surface of the core, but rather an enlargement of the core. Moreover, if one examines the final beads, layers cannot be seen in the active core, whereas actual layers can be distinctively seen in the membrane. In one embodiment, the preferred number of cycles is between 70 and 140.

Thereafter, the product may be air dried in hot air or may be passed through a desiccation enclosure. The microgranules may be sieved and checked for humidity and grain size.

Numerous types of coatings within the scope of the present invention may be used to make the inner and outer membranes in accordance with the invention. Such different coatings as envisioned by the present invention enable the achievement of products which are at least biologically equivalent to prior art products such as disclosed in U.S. Pat. No. 4,721,619.

The inner membrane layers are preferably comprised of ethylcellulose and a lubricant, such as talc. Other acceptable lubricants are calcium stearate, zinc stearate or magnesium stearate. In some cases the inner membrane may be a polymer such as EUDRAGIT RS.

The outer membrane coating comprises a water insoluble pharmaceutically acceptable polymeric material which is applied by dissolving the material in a suitable solvent. In addition, the membrane may contain either or both a plasticizer such as diethylphthalate and a lubricant such as talc or other lubricants noted above. In the preferred embodiment, the water insoluble polymeric material of the outer membrane coating is EUDRAGIT S100. Other suitable plasticizers are polyethylene glycols, dibutyl phthalate or triacetin. The outer membrane coating may be a single layer or up to five or more layers.

As should be readily apparent to those skilled in the pharmaceutical art, EUDRAGIT S is the trademark for the polymer which is slightly permeable to diltiazem and water. EUDRAGIT polymers are polymeric lacquer substances based on acrylic and/or methyacrylic acid esters. These products are described further in the EUDRAGIT brochures of Messrs. Rohm Pharma GmbH (1985 et seq.). Other suitable water insoluble polymers are cellulose acetate phthalate, EUDRAGIT L, EUDRAGIT RS and AQUACOAT.

In the present invention, the solution of ethylcellulose for the inner membrane layers is prepared utilizing a solvent. These ingredients may be applied by conventional methods such as by conventional pan coating with a lubricant being poured into the coating pan. The solution may be applied while simultaneously projecting the talc. Drying may be performed in hot air, after which the pellets are sieved, and humidity and grain size are checked. Preferably the number of layers of the inner membrane solution that are applied is between 1 and 20.

The outer membrane coating is preferably applied by a conventional method utilizing a fluidized air-bed equipped with a Wurster column in a continuous process. In this equipment, the appropriate outer membrane is sprayed onto the ethylcellulose coated cores. The outer membrane coating solution may contain one or more of the water insoluble polymers dissolved in a suitable solvent such as ethanol, acetone or isopropanol, or a mixture thereof, in the presence of other additives such as a lubricant, e.g., talc, and a plasticizer such as diethylphthalate. The coating obtained is very homogeneous and regular. The outer membrane coating may be from 1 to 5 layers or more. Drying may be performed in hot air, after which the pellets are sieved, and humidity and grain size are checked. Thereafter the product may be put into capsules or tablets.

At no time is shellac used in either membrane. Shellac is unsatisfactory for several reasons, including decreasing the shelf life of the product.

The characteristics of the water insoluble inner and outer membranes of the product obtained this way should enable the diltiazem hydrochloride to be released into an aqueous medium of the following intervals as measured using a paddle apparatus according to United States Pharamcopeia XXII:

(a) from 15 to 40% of the total diltiazem is released after 4 hours of measurement;
(b) from 40 to 70% of the total diltiazem is released after 8 hours of measurement;
(c) from 50 to 85% of the total diltiazem is released after 12 hours of measurement; and
(d) from 70 to 100% of the total diltiazem is released after 24 hours of measurement.

From the foregoing it can be seen that the preferred membrane of the present invention contains a combination of two or more water insoluble polymers, one of which is soluble in neutral to weakly alkaline media. One of these polymers, ethylcellulose is water insoluble and insoluble in neutral to weakly alkaline media. Another polymer, EUDRAGIT S100, is water insoluble, but soluble in neutral to weakly alkaline media.

In the preferred embodiment there is approximately 10% of the methacrylic acid copolymer, 0.6% ethylcellulose N7, 1.25% plasticizer and 6.5% talc. These percentages as well as all other percentages set forth hereinabove are weight percentages.

The weight ratio of the water insoluble, pH dependent polymer, such as EUDRAGIT S100 to diltiazem is in the range of 0.15:1 to 0.24:1. The ratio of the water insoluble, pH independent polymer, such as ethylcellulose, is in the weight ratio range of 0.009:1 to 0.014:1. The ratio of lubricant to diltiazem is in the weight ratio range of 0.1:1 to 0.15:1. The ratio of plasticizer to diltiazem is in the weight ratio range of 0.02:1 to 0.03:1.

MANUFACTURING EXAMPLE I

Diltiazem hydrochloride (6.0 kg) was sieved through a 1.25 mm screen. The powder was applied to starch-/sugar seeds (0.4 mm to 0.7 mm diameter) (3.6 kg) in a coating pan using a binding solution of 20% PVP K 30 in alcohol.

The seeds were coated with a measured volume of binding solution followed by dusting on of a measured weight of powder. The coated seeds were allowed to dry and the layer step repeated until all of the powder had been applied. The coated seeds were then dried at approximately 25° C. overnight. After the layering of the active ingredient, the seeds were control tested before coating.

The active cores being prepared, were then surrounded by an inner or first membrane by applying 12 coats of a solution consisting of 10% EUDRAGIT RS in an acetone/isopropanol solution in a coating pan. Talc was poured in the coating pan during this step. EUDRAGIT RS is an anionic polymer synthesized from acrylic and methacrylic acid ester with a low content of quaternary ammonium groups. The ammonium groups are present as salts and give rise to the permeability of the lacquer films. They afford water-insoluble, but permeable, film coatings.

The beads so obtained were then introduced into a fluidized air-bed equipped with a Wurster column. In this equipment, a polymeric solution mixed with diethylphthalate and talc consisting an outer or second membrane was sprayed onto the beads. The polymeric solution consisted of: 7.5% EUDRAGIT S in acetone/isopropanol 70% (w/w) and 7.5% EUDRAGIT L in acetone/isopropanol 30% (w/w).

MANUFACTURING EXAMPLE II

Example I was repeated except that the polymeric solution used in the second membrane consisted of: 7.5% EUDRAGIT L in acetone/isopropanol 25% (w/w) and 7.5% EUDRAGIT S in acetone/isopropanol 75% (w/w).

MANUFACTURING EXAMPLE III—PREFERRED EMBODIMENT

Example I was repeated except that the polymeric solution used in the first membrane was ethylcellulose instead of EUDRAGIT RS and the polymeric solution used to apply the outer membrane consisted of EUDRAGIT S alone.

DISSOLUTION DATA

The product of Example III was utilized in clinical testing of humans. The results obtained which relate to the industrial batch are as follows:

| Times (h) | Mean (6 rep) % | Standard deviation | cv % |
|---|---|---|---|
| pH = 6.5; USP XXII | | | |
| 1 | 2.14 | 0.39 | 18.42 |
| 2 | 6.06 | 0.53 | 8.79 |
| 3 | 11.65 | 0.69 | 5.89 |
| 4 | 18.18 | 0.74 | 4.06 |
| 5 | 25.15 | 0.90 | 3.57 |
| 6 | 32.24 | 0.95 | 2.94 |
| 7 | 39.39 | 0.80 | 2.02 |
| 8 | 45.66 | 0.94 | 2.06 |
| pH = 7.4; USP XXII | | | |
| 1 | 31.00 | 3.82 | 12.32 |
| 2 | 87.13 | 2.22 | 2.54 |
| 3 | 98.43 | 1.40 | 1.43 |
| 4 | 101.88 | 1.17 | 1.15 |
| pH = 8.5; USP XXII | | | |
| 1 | 99.66 | 2.06 | 2.06 |
| 2 | 98.81 | 1.16 | 1.17 |
| 3 | 94.45 | 0.84 | 0.89 |
| Water | | | |
| 4 | 16.68 | 1.77 | 10.58 |
| 8 | 43.96 | 0.96 | 2.19 |
| 12 | 62.47 | 0.78 | 1.25 |
| 24 | 86.46 | 1.95 | 2.26 |

| Times (h) | Mean (3 rep) % |
|---|---|
| Water | |
| Results of the dissolution tests/First manufacturing example | |
| 4 | 32.83 |
| 8 | 62.66 |
| 12 | 77.81 |
| 24 | 94.92 |
| Results of the dissolution tests/Second manufacturing example | |
| 4 | 37.71 |
| 8 | 66.89 |
| 12 | 80.15 |
| 24 | 95.60 |

Results of the dissolution tests/Third manufacturing example (relating to a laboratory batch)

| Times (h) | Mean (6 rep) % | Standard deviation | cv % |
|---|---|---|---|
| 4 | 26.09 | 1.76 | 6.76 |
| 8 | 43.96 | 1.28 | 2.91 |
| 12 | 57.16 | 1.08 | 1.90 |
| 24 | 78.43 | 0.99 | 1.26 |

EXAMPLES OF CAPSULES

The following is an example of a 60 mg diltiazem hydrochloride sustained release capsule:

| | |
|---|---|
| Diltiazem HCl, USP | 60 mg |
| Sugar spheres, NF | 33.3 mg |
| Povidone, USP | 3.9 mg |
| Methacrylic acid copolymer, NF | 11.9 mg |
| Ethylcellulose, NF | 0.7 mg |
| Diethyl phthalate, NF | 1.5 mg |
| Talc, USP | 7.5 mg |
| Isopropyl alcohol, USP | non-residual |
| Acetone | non-residual |
| Alcohol | non-residual |
| TOTAL | 118.8 mg |

Gelatin Capsule #3, colorants red iron oxide, titanium dioxide.

The following example for the 90 mg diltiazem hydrochloride sustained release capsule is provided:

| | |
|---|---|
| Diltiazem HCl, USP | 90 mg |
| Sugar spheres, NF | 50 mg |
| Povidone, USP | 5.9 mg |
| Methacrylic acid copolymer, NF | 17.8 mg |
| Ethylcellulose, NF | 1 mg |
| Diethyl phthalate, NF | 2.2 mg |
| Talc, USP | 11.2 mg |
| Isopropyl alcohol, USP | non-residual |
| Acetone | non-residual |
| Alcohol | non-residual |
| TOTAL | 178.1 mg |

Gelatin Capsule #2, colorants red iron oxide, yellow iron oxide, titanium dioxide.

The following example for the 120 mg diltiazem hydrochloride sustained release capsule is provided:

| | |
|---|---|
| Diltiazem HCl, USP | 120 mg |
| Sugar spheres, NF | 66.6 mg |
| Povidone, USP | 7.8 mg |
| Methacrylic acid copolymer, NF | 23.8 mg |
| Ethylcellulose, NF | 1.4 mg |
| Diethyl phthalate, NF | 3 mg |
| Talc, USP | 15 mg |
| Isopropyl alcohol, USP | non-residual |
| Acetone | non-residual |
| Alcohol | non-residual |
| TOTAL | 237.6 mg |

Gelatin Capsule #1, colorants red iron oxide, yellow iron oxide, titanium dioxide.

In the above three capsule examples, it should be readily apparent to those skilled in the art that the total amount of inactive ingredients per capsule will vary from batch to batch, based on the quantity of pellets required to deliver the particular number of milligrams of diltiazem HCl per capsule. The amount of excipients may be varied by ±20%. The amount of pellets per capsule may be determined, prior to encapsulation, based on a diltiazem hydrochloride assay result for the respective lot of diltiazem hydrochloride sustained-release pellets.

Without further elaboration the foregoing will so fully illustrate our invention that others may, by applying current or future knowledge, adapt the same for use under various conditions of service.

We claim:

1. A sustained release diltiazem formulation for oral administration comprising a pellet substantially free of an organic acid which may have an irritating effect, the said pellet having:
    (a) a central inactive sphere;
    (b) a plurality of alternating first and second layers surrounding the sphere to form a core, the first layer comprising a water soluble pharmaceutically acceptable polymeric material and the second layer comprising diltiazem or a pharmaceutically acceptable salt thereof; and
    (c) an outer coating comprising
        first inner membrane layers applied to said core, said first inner membrane layers comprising a first water insoluble pharmaceutically acceptable polymer, and
        a single outer membrane forming a relatively thick and homogeneous layer surrounding said first inner membrane layers and comprising a second water insoluble pharmaceutically acceptable polymeric material different from said first water insoluble pharmaceutically acceptable polymer;
    the number of the first inner membrane layers and the single outer membrane being selected to be effective to permit the release of the diltiazem from the pellet at a rate allowing controlled absorption thereof over a twelve hour period following oral administration, the rate being measured in vitro as a dissolution rate of the pellet which when measured in a type 2 dissolution apparatus according to United States Pharmacopeia XXII substantially corresponds to the following dissolution pattern:
    (a) from 15 to 40% of the total diltiazem is released after 4 hours of measurement;
    (b) from 40 to 70% of the total diltiazem is released after 8 hours of measurement;
    (c) from 50 to 85% of the total diltiazem is released after 12 hours of measurement;
    (d) from 70 to 100% of the total diltiazem is released after 24 hours of measurement.

2. The formulation of claim 1 wherein the water soluble pharmaceutically acceptable polymeric material is selected from the group consisting of polyvinylpyrrolidone, polyethyleneglycol, polyvinyl alcohol and their mixtures.

3. The formulation of claim 1 wherein the first water insoluble pharmaceutically acceptable polymeric material is ethylcellulose and wherein the second water insoluble pharmaceutically acceptable polymeric material is selected from the group consisting of a copolymer of acrylic and methacrylic acid esters and cellulose acetate phthalate.

4. The formulation of claim 1 including a lubricant in said first membrane layers and in said single outer membrane, said lubricant being selected from the group consisting of talc, calcium stearate, zinc stearate and magnesium stearate.

5. The formulation of claim 1 including a plasticizer in said single outer membrane.

6. The formulation of claim 5 wherein said plasticizer is selected from the group consisting of diethylphthalate, polyethyleneglycols, dibutyl phthalate and triacetin.

* * * * *